United States Patent
Deviere et al.

(10) Patent No.: US 8,684,912 B2
(45) Date of Patent: Apr. 1, 2014

(54) DEPLOYABLE ENDOSCOPIC SUPPORT DEVICE

(75) Inventors: Jacques Deviere, Genappe (BE); Nicolas Cauche, Brussels (BE); Alain Delchambre, Brussels (BE); Sylvie Evrard, Brussels (BE)

(73) Assignee: Université Libre de Bruxelles, Brussels (BE)

( * ) Notice: Subject to any disclaimer, the term of this patent is extended or adjusted under 35 U.S.C. 154(b) by 1650 days.

(21) Appl. No.: 11/640,705

(22) Filed: Dec. 18, 2006

(65) Prior Publication Data
US 2007/0197862 A1 Aug. 23, 2007

Related U.S. Application Data

(63) Continuation of application No. PCT/BE2005/000098, filed on Jun. 6, 2005.

(30) Foreign Application Priority Data

Jun. 18, 2004 (EP) .................................... 04447144

(51) Int. Cl.
A61B 1/00 (2006.01)
(52) U.S. Cl.
USPC ........... 600/114; 600/104; 600/106; 600/127; 600/129
(58) Field of Classification Search
USPC ......... 600/101, 102, 104, 121–125, 127, 129, 600/106, 107, 114–115, 139–152; 604/95.01–95.05, 528; 606/1
See application file for complete search history.

(56) References Cited

U.S. PATENT DOCUMENTS

| | | | | |
|---|---|---|---|---|
| 4,290,421 A | * | 9/1981 | Siegmund | 600/141 |
| 5,217,001 A | * | 6/1993 | Nakao et al. | 600/123 |
| 6,179,776 B1 | | 1/2001 | Adams et al. | |
| 6,352,503 B1 | * | 3/2002 | Matsui et al. | 600/104 |
| 6,613,002 B1 | * | 9/2003 | Clark et al. | 600/593 |
| 6,878,106 B1 | * | 4/2005 | Herrmann | 600/104 |
| 2003/0023142 A1 | * | 1/2003 | Grabover et al. | 600/143 |
| 2003/0114732 A1 | | 6/2003 | Schneiderman et al. | |
| 2003/0195387 A1 | * | 10/2003 | Kortenbach et al. | 600/104 |
| 2004/0138525 A1 | * | 7/2004 | Saadat et al. | 600/104 |
| 2005/0085691 A1 | * | 4/2005 | Nakao | 600/128 |

FOREIGN PATENT DOCUMENTS

| | | | | |
|---|---|---|---|---|
| JP | 06125868 A | * | 5/1994 | |
| JP | 2003/245241 A | | 9/2003 | |
| WO | WO0048506 A | * | 8/2000 | |

OTHER PUBLICATIONS

English translation of JP06125868.*
International Search Report issued in PCT Application No. PCT/BE2005/000098, dated Nov. 15, 2005.

* cited by examiner

Primary Examiner — Matthew J Kasztejna
Assistant Examiner — Ryan Henderson
(74) Attorney, Agent, or Firm — Knobbe, Martens, Olson & Bear LLP

(57) ABSTRACT

An endoscopic support device configured to support an endoscope during a surgical procedure is disclosed. The endoscopic support device has a connection ring with a height smaller than its diameter and configured to be in an open or deployed position and in a closed or non-deployed position. The support device also has at least two guiding elements, an orientation component, and extension means for manipulating the ring between the deployed and non-deployed positions.

27 Claims, 16 Drawing Sheets

DEPLOYABLE ENDOSCOPIC SUPPORT DEVICE

REFERENCE TO RELATED APPLICATIONS

This application claims priority to and is a continuation of PCT International Application Number PCT/BE2005/000098, filed on Jun. 6, 2005, which claims priority under 35 U.S.C. §119 to EP patent application 04447144.9 filed on Jun. 18, 2004. The disclosures of the above-described applications are hereby incorporated by reference in their entirety.

BACKGROUND

1. Field of the Invention

The present invention relates to a device that can be used in endoscopy, and more particularly, to an endoscopic device or endoscopic support intended to permit precise in situ positioning of an endoscope and of associated surgical instruments. However, the present device may also be adapted to viewing systems other than an endoscope, which are familiar to a person skilled in the art.

2. Description of the Related Technology

Therapeutic endoscopy has developed considerably over the past twenty years. Performed either via the oral or anal route, therapeutic endoscopy makes it possible, by means of an instrument called an "endoscope", to gain direct access to the interior of the digestive tract without the need to open the abdominal wall or create a passage through the peritoneal cavity, thus enhancing patient comfort and reducing patient morbidity.

More specifically, an endoscope is conventionally in the form of a flexible tube comprising an optics channel and one or more operating channels allowing one or more surgical instruments to be introduced with a view to perform a surgical procedure in situ, that is to say in the area of the target (cavity) that is to be treated in the body of the patient.

However, such an arrangement of the operating channels parallel to the endoscope considerably limits the spatial movements of the surgical instruments relative to one another and relative to the endoscope, and an effective solution to this problem would be desirable.

The document U.S. Pat. No. 6,352,503 B1 has proposed a surgical endoscopic apparatus comprising an endoscope provided with an insertion zone inside which a observation device is inserted, and at least two insertion arms in which a surgical instrument is inserted, said apparatus having the particular feature of additionally comprising a positioning device for varying one or other of the distances between the insertion zone of the endoscope, the first insertion arm and the second insertion arm in a direction substantially orthogonal to the axis of the insertion zone of the endoscope. In this embodiment, the positioning device is in the form of an inflatable balloon or also in the form of an extensible "basket".

However, in this solution, the spatial movements of the surgical instruments are still quite restricted.

The document U.S. Pat. No. 6,179,776 B1 describes a device that can be coupled to an endoscope and is in the form of a flexible sheath that can be engaged on the endoscope. This sheath has a length which is such that it envelops the endoscope along essentially its entire length. The device is provided with lumens which extend along the walls of the sheath and at the distal end of which surgical instruments can be fixed. The device is connected to the endoscope prior to insertion of the device into the patient's body. Once the device connected to the endoscope has reached its target site in situ, under the action of control means, the distal end of the lumens is capable of undergoing a deflection, the extent of which is regulated, thereby permitting a positioning and orientation of the surgical instruments relative to the site that is to be treated.

SUMMARY OF CERTAIN INVENTIVE ASPECTS

Certain inventive aspects relate to an endoscopic support comprising a connection ring for connecting to an endoscope, and at least two operating arms which are attached to said connection ring and through each of which at least one surgical instrument can be passed, each of said operating arms having at least a first degree of freedom in rotation according to which each of the operating arms can be oriented independently of the other.

More precisely, one inventive aspect relates to an endoscopic device or support which is deployable and comprises:

a connection ring for connecting to an endoscope, said ring corresponding to an element which is such that, in the deployed position of said device or of said support, the height of said element is smaller than its diameter, and said element has a central opening such that said ring can be connected to the distal end of an endoscope;

at least two guiding means or operating arms that can be attached to said connection ring, each of said operating arms being able to receive at least one surgical instrument and to be oriented, independently of the other arm, in at least two degrees of freedom in rotation in a same first orientation plane in such a way that, when a surgical instrument is fixed to said arm, the latter is able to confer on said surgical instrument a displacement in at least two dimensions in the space;

orientation means designed to orient said guiding means or operating arms in their degrees of freedom;

extension means for converting said endoscopic device or support from a non-deployed position to a deployed position.

The device of certain embodiments therefore has the characteristic of being deployable and, more precisely, its connection ring is deployable.

The first orientation plane may be defined by the two main axes of said operating arms.

Each of said arms may have a third degree of freedom in rotation, such that each of said arms can be oriented in this degree of freedom in a second orientation plane.

The second orientation plane of the operating arms may be defined by the main axis of said operating arm and a second axis corresponding to the axis substantially perpendicular to the first orientation plane.

Each of said arms additionally may have a degree of freedom in translation corresponding to the degree of freedom in translation along the main axis of said arm.

Each of said arms additionally may have a degree of freedom in rotation corresponding to the degree of freedom in rotation along the main axis of said arm.

Advantageously, the extension means of the device may be situated at least in part in the area of the connection ring.

Advantageously, the connection ring may comprise means for remote connection to the endoscope.

The means for connection to the endoscope and the extension means of the device may be the same.

In its deployed position, and when not in operation, the device according to certain embodiments has a maximum volume in situ defined as the volume for which the device presents in situ a maximum dimensional and mechanical stability.

In its deployed position, and when not in operation, said device may have a in situ maximum volume which is greater than the minimum volume of said device in the non-deployed position by at least about 10%, at least about 20%, at least about 30%, at least about 40%, at least about 50%, at least about 60%, at least about 70%, at least about 80%, at least about 90%, at least about 100%, at least about 200%, at least about 300%, at least about 500%, at least about 1000%, at least about 2000%.

Advantageously, in its deployed position, and when the device is not in operation, the operating arms may be oriented substantially perpendicularly to the plane of the ring and are substantially parallel to one another.

The device according to some embodiments can be coupled to manual or automatic actuation or control means for controlling the actuation of the orientation means and/or the actuation of the extension means.

According to some embodiments, the connection ring comprises a flexible membrane and a cable called the connection cable, said ring being folded up on itself in the non-deployed position of the device and being deployed in the deployed position of said device.

The extension means may comprise said connection cable and a cable called the fold-back cable, and said extension means can be actuated by way of rigid guides.

According to some embodiments, the connection ring for connecting to the endoscope is in the form of a rigid structure with a main axis.

The extension means of the support may correspond to a pivoting device which is able to pivot said ring about its main axis by a certain angle.

In some embodiments, the orientation means comprise a set of cables which are situated in the area of the operating arms and can be actuated so as to move.

According to some embodiments, the connection ring for connecting to the endoscope comprises an inflatable membrane, the ring being not inflated in the non-deployed position of the device, and being inflated in the deployed position of the device.

In some embodiments, the means for orientation of the operating arms are in the form of a fluid circulation circuit comprising at least compartments situated in the area of the ring and able to be filled by a fluid according to an adjustable filling level.

In some embodiments, the orientation means of the operating arms are in the form of a fluid circulation circuit comprising at least compartments situated in the area of the operating arms and able to be filled by a fluid according to an adjustable filling level.

Advantageously, the orientation means of the operating arms may be in the form of a fluid circulation circuit comprising compartments situated in the area of the operating arms and in the area of the connection ring, said compartments being able to be filled by a fluid according to an adjustable filling level.

According to some embodiments, the two operating arms are flexible.

According to some embodiments, the two operating arms are arranged opposite each other in relation to the diameter of the connection ring.

In some embodiments, the operating arms are provided with optical markers.

In some embodiments, at least some of the elements of the device are single-use.

Alternatively, the device can be cleaned and can be reused at least one time after cleaning.

Another inventive aspect relates to an endoscopy kit comprising an endoscopic device or support, and means for automatic actuation or means for manual actuation of the orientation means of the operating arms and/or of the extension means of the support.

Some embodiments also related to an endoscopy kit comprising an endoscopic device and an endoscope and/or at least one surgical instrument.

Some embodiments also relate to a method for performing a surgical procedure at a specific site in the body of a patient, said method comprising the following steps:
- the various elements of the device according to any one of the preceding claims are assembled,
- said device, in the non-deployed position, is introduced by an endoluminal route into the body of the patient up to the specific site that is to be treated,
- the device is deployed in situ with the aid of the extension means,
- an endoscope is connected in situ to said device, via the distal end of said endoscope, setting the height at the distal end of said endoscope at which the connection is made,
- one or more surgical instruments are fixed on one or more of the guiding means or operating arms,
- the surgical treatment as such is then performed by controlling, via the orientation means of the operating arms, the in situ orientation of the operating arms in space and, consequently, the spatial displacement of the instruments, under the control of the actuation device;
- if necessary, during the procedure, the orientation of the endoscope is varied in relation to the site to be treated, and the surgical instruments on the operating arms of the endoscopic device are varied,
- once the treatment has been completed, the surgical instruments are removed from the endoscopic device, said endoscopic device and the endoscope are disconnected in situ, under the control of the extension means, the endoscopic device is converted in situ from a deployed position to a non-deployed position, and the endoscopic device is removed from the patient's body.

In some embodiments, at the end of the procedure, the endoscopic device is disconnected and then it is taken apart or it is cleaned for reuse.

BRIEF DESCRIPTION OF THE DRAWINGS

A first variant of the endoscopic support or device according to one embodiment is illustrated in FIGS. 1a, 1b, 2a, 2b, 3a and 3b.

FIG. 4 (general view) and FIG. 5 (detail of the connection ring, seen from above) correspond to the support without endoscope and in the non-deployed position. FIGS. 6 to 10 show different general and detailed views of this same support when in the deployed position and connected to an endoscope.

Figure 23:
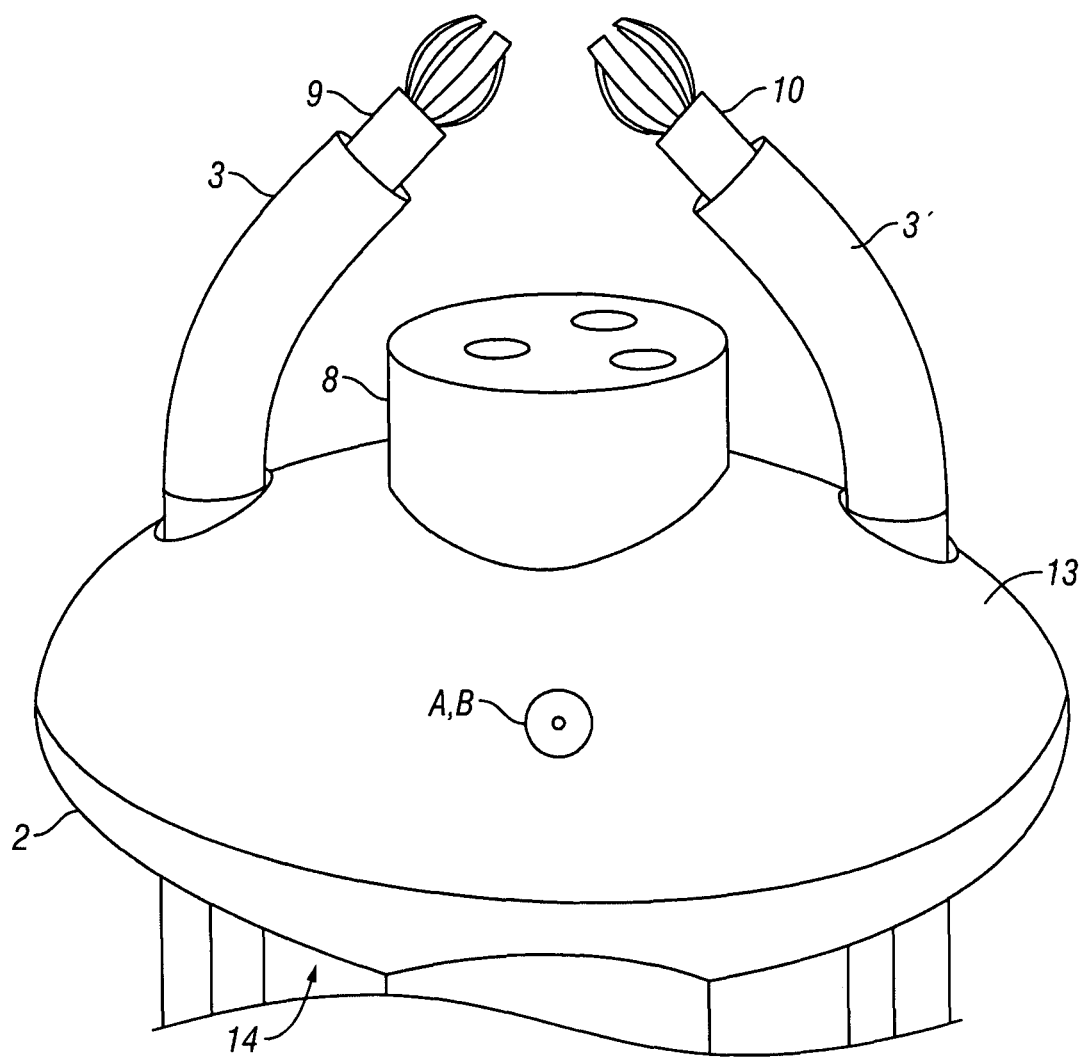

Another embodiment of an endoscopic support is illustrated in FIG. 23.

Yet another embodiment is shown in FIGS. 11 to 22.

Figure 11:
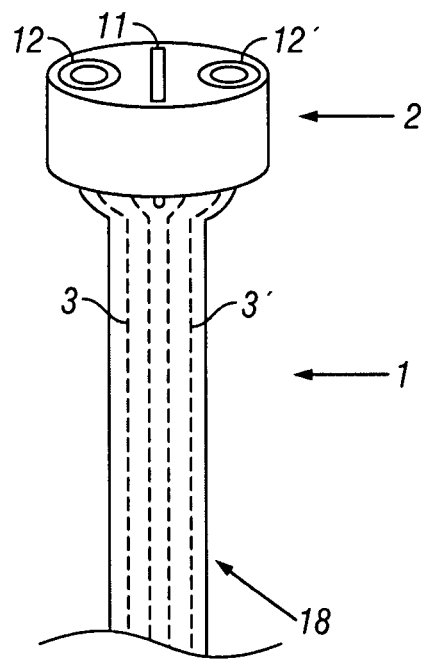
Figure 11:
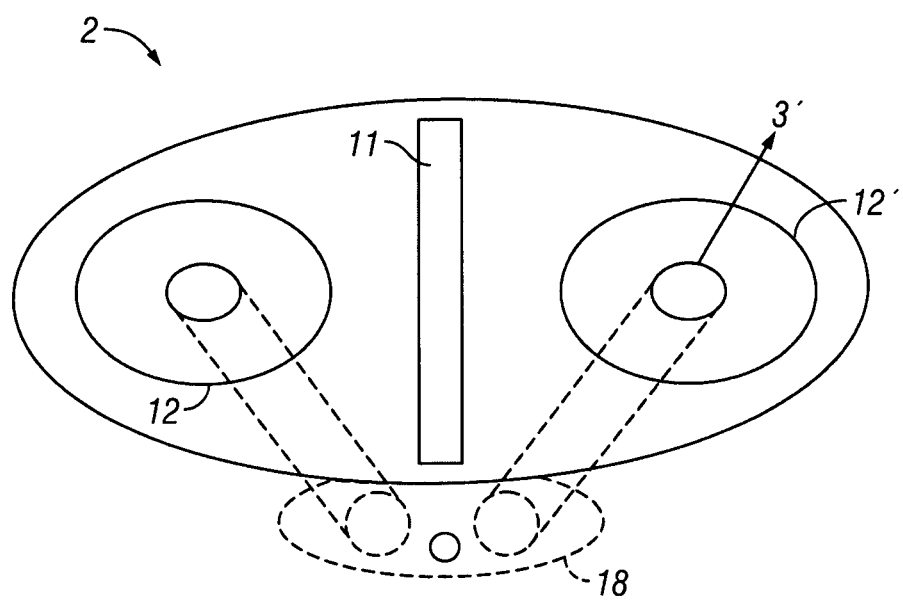
Figure 12:
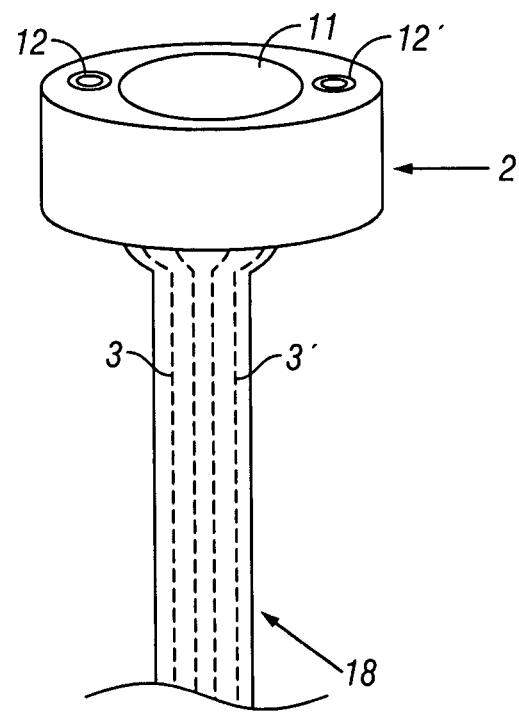
Figure 12:
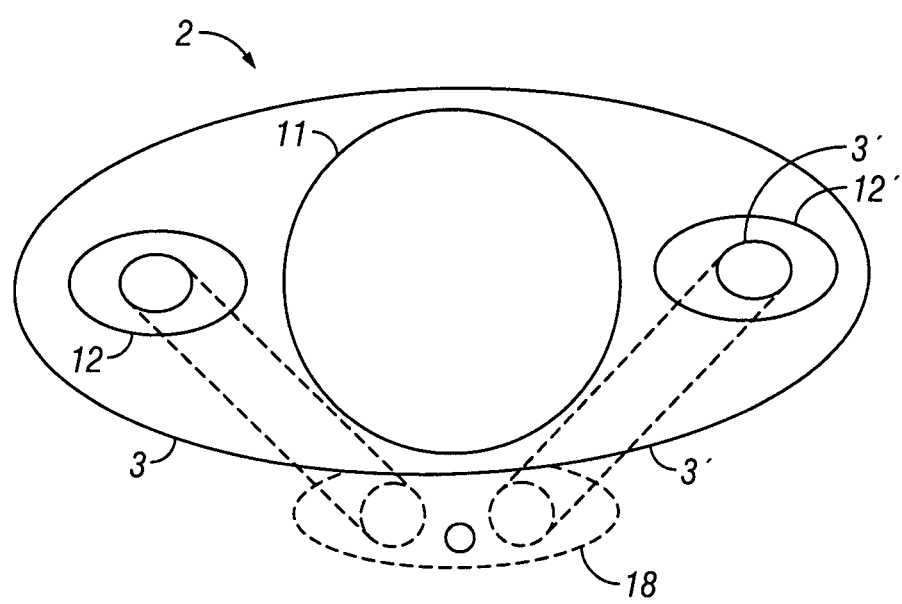
Figure 13:
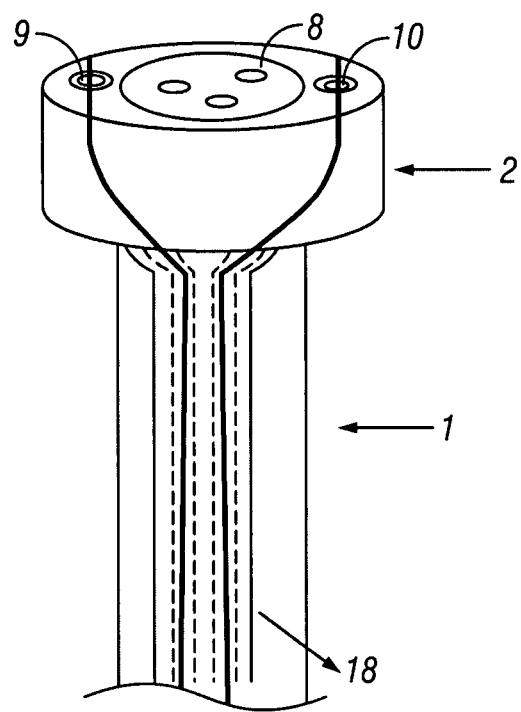
Figure 13:
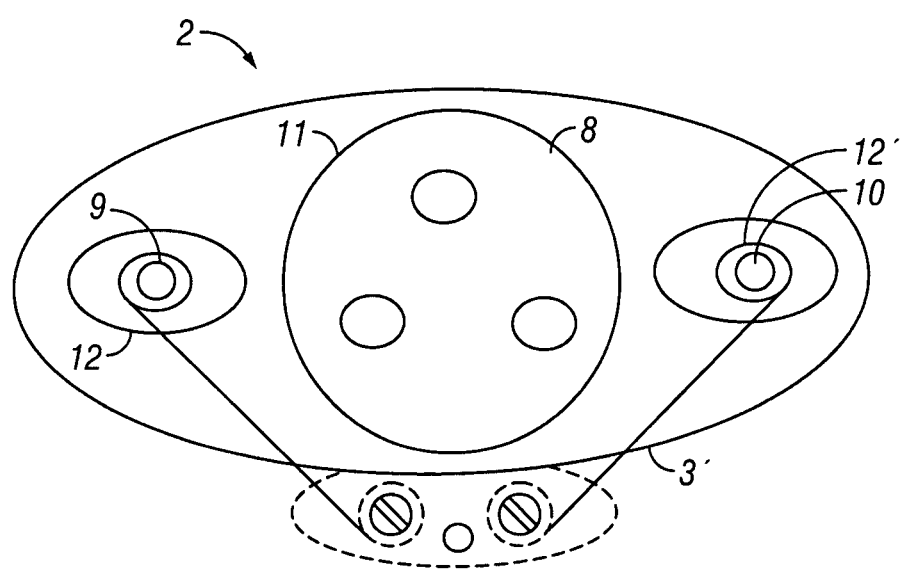
Figure 14:
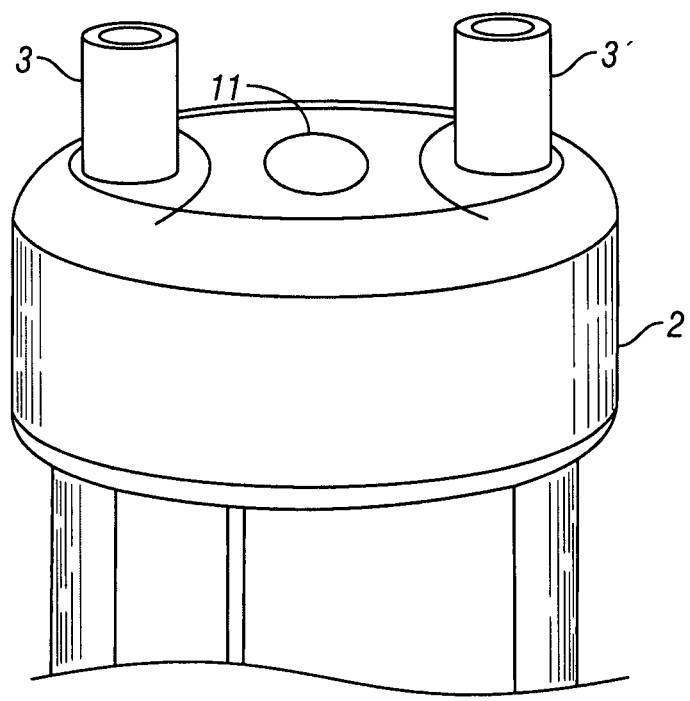
Figure 15:
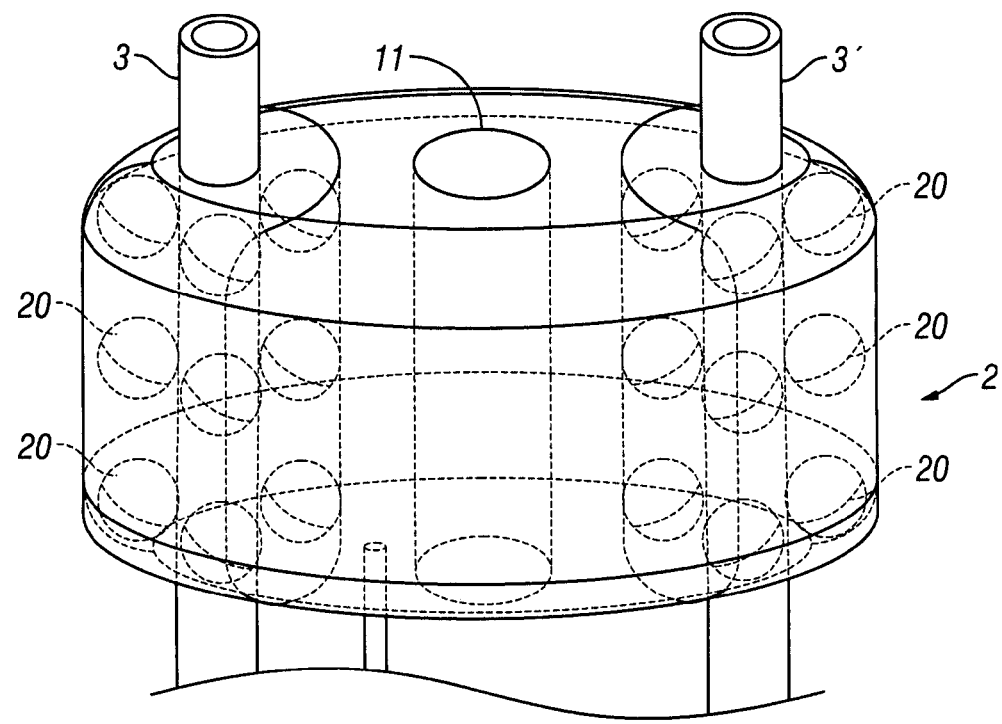

More specifically, FIGS. 11 to 13 relate to a first configuration of the endoscopic support or device.

FIG. 11 shows a support according to this configuration, in the non-deployed position (front view on the left; top view on the right).

FIG. 12 shows this same support, but in the deployed position (front view on the left; top view on the right).

FIG. 13 shows how an endoscope and surgical instruments can be connected to this support.

Figure 16:
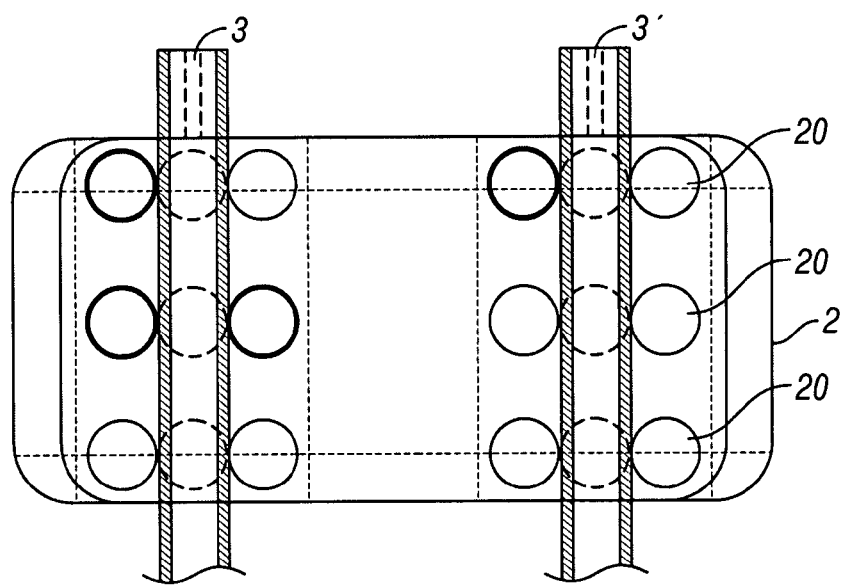
Figure 17:
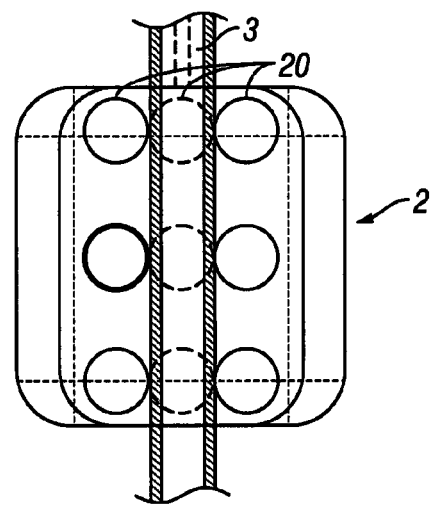
Figure 18:
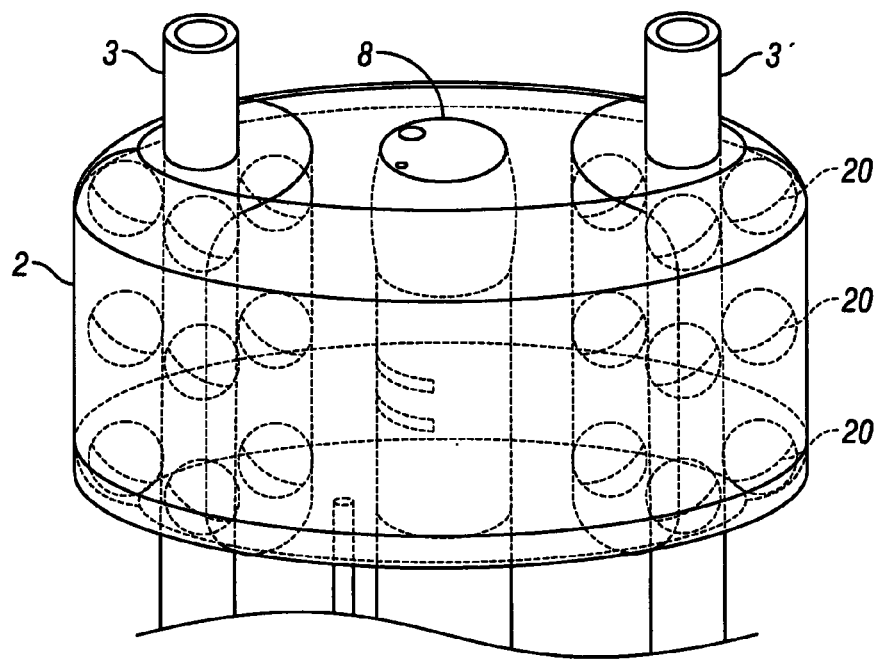
Figure 19:
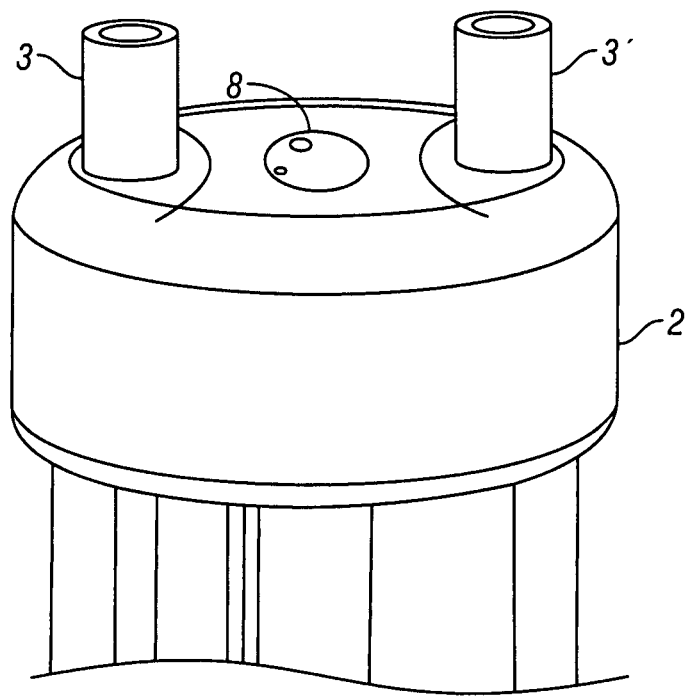

FIGS. 14 to 19 also relate to another embodiment. Compared to FIGS. 11 to 13, they correspond to an improved model of the support in three dimensions (FIGS. 14, 15, 18, 19) or in two dimensions (FIGS. 16, 17). In FIGS. 14 to 17, the support is deployed, but not connected to an endoscope. In FIGS. 18 and 19, the support is deployed and is connected to an endoscope.

It will be noted that FIGS. 15 to 18 show the structure of the connection ring in this embodiment.

Figure 20:
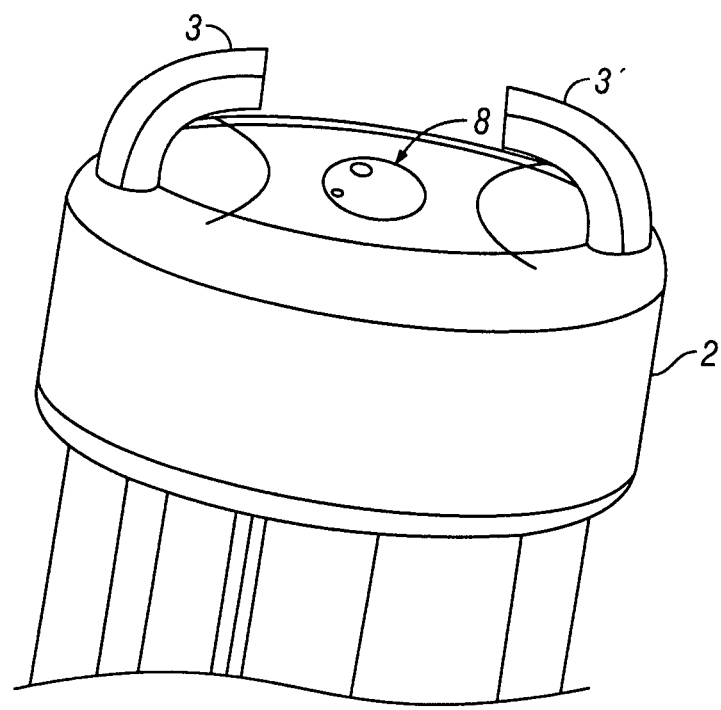
Figure 21:
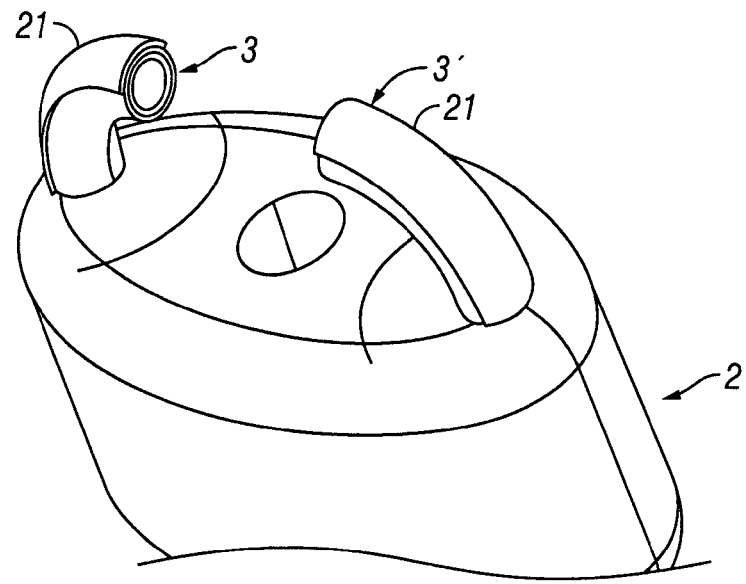
Figure 22:
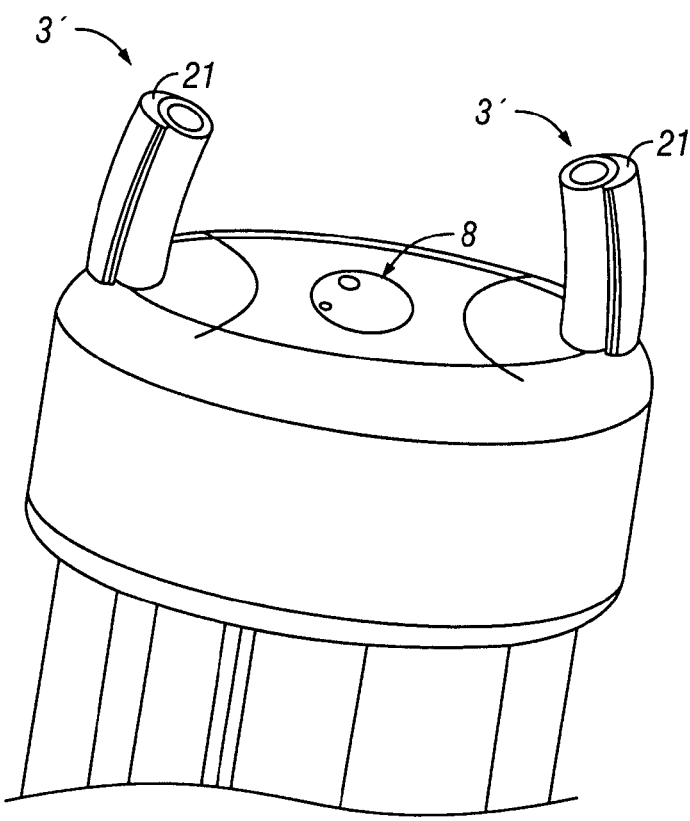

FIGS. 20 to 22 relate to a second configuration of the endoscopic support or device according to some embodiments. This configuration differs from the first configuration in that the operating arms are at least partly curved. In FIGS. 20 and 22, the support is in the deployed position and connected to an endoscope. In FIG. 21, the support is also deployed, but is not connected to an endoscope. FIG. 21 also shows the presence of a pocket or of compartments in the area of the operating arms, and these help form the means for orientation of said arms.

DETAILED DESCRIPTION OF CERTAIN INVENTIVE EMBODIMENTS

Definitions:

It will be noted that, in the present description, the words "positioning" and "orientation" are related to one another.

It is therefore be understood that, in the present description, a position and/or an orientation of the operating arms corresponds to a precise set of spatial coordinates.

As will also be understood in the present description, the endoscopic support according to certain embodiments makes it possible to position and/or orient an endoscope and surgical instruments at a certain height in the digestive tract of a patient, but also, once this height set, to precisely adapt the position and/or orientation of the operating arms and of the surgical instruments.

The notion of "degree of freedom" of a system, such as it is used in the present discussion, corresponds to that commonly used by a person skilled in mechanics and designates a priori both a degree of freedom in rotation and a degree of freedom in translation.

The notion of "connection position" of the support is a particular configuration of the support in which it can be connected to an endoscope. This connection position of the support corresponds itself to a certain configuration of the connection ring of the support.

The endoscopic device or support according to certain embodiments, which essentially comprises the connection ring plus the operating arms, is "deployable", that is to say it has the capacity to be deployed.

In the rest of the description, the terms "operating arms" and "guiding means" are equivalent. The expression "guiding means" refers to the function of the operating arms, which is to guide or confer spatial movements on the surgical instruments that are fixed on these arms in relation to the site of the human body to be treated.

The operating arms thus are used both to support and to guide the surgical instruments. Each operating arm can receive one or more surgical instruments and can be adapted to a wide range of surgical instruments that differ in form, size, weight, composition, etc.

In the rest of the description, the terms "connection ring for connecting to an endoscope" or "connection ring" or "ring" are equivalent and correspond to an element of the endoscopic device of which one of the characteristics is that, when the endoscopic device is deployed, the height of said element is smaller than its diameter.

The term "deployment" of the endoscopic device or support according to certain embodiments signifies the action of spreading-open of said device or of said support. This spreading-open is such that the volume within which the support can be circumscribed, and which is minimal prior to deployment, is subject in situ to an increase of at least about 10%, at least about 20%, at least about 30%, at least about 40%, at least about 50%, at least about 60%, at least about 70%, at least about 80%, at least about 90%, at least about 100%, at least about 200%, at least about 300%, at least about 500%, at least about 1000%, at least about 2000%.

In the French priority application EP 04447144.9, the terms "deployed" and "unfolded" have been used for one another. For the sake of exactness, however, we will consider in the present discussion that the term "deployed" encompasses the term "unfolded", which refers to a spreading-open of the device by a mechanical effect, and the term "inflated", which refers to a spreading-open of the device by a hydraulic and/or pneumatic effect.

The term "deployed" is appropriate since it is close to the characteristic of the device. For this reason, the present description will use the term "deployed".

In the French priority application EP 04447144.9, the terms "non-deployed" and "folded up" have been used for one another. For the sake of exactness, however, we will consider in the present discussion that the term "non-deployed" encompasses the term "folded up", which refers to a non-spreading-open of the device by a mechanical effect, and the term "non-inflated", which refers to a non-spreading-open of the device by a hydraulic and/or pneumatic effect.

The term "non-deployed" is appropriate since it is close to the characteristic of the device according to some embodiments. For this reason, the present description will use the term "non-deployed".

For the support according to certain embodiments, a non-deployed position is defined for which the volume within which the outlines of the support are circumscribed is minimal.

This minimal volume is calculated in order to respect certain constraints of use. More precisely, this minimal volume is calculated in order to permit insertion of the support into the patient's body by an endoluminal route, for example through the esophagus.

For this same support, a deployed position is defined for which the volume within which the outlines of the support are circumscribed represents at least about 110%, at least about 120%, at least about 130%, at least about 140%, at least about 150%, at least about 160%, at least about 170%, at least about 180%, at least about 190%, at least about 200%, at least about 300%, at least about 400%, at least about 500%, at least about 1100%, at least about 2100% of the minimal volume of the support in the non-deployed position. This maximum volume corresponds to the volume of the support when it is deployed in situ. In the deployed position, the support according to certain embodiments has a conformational and mechanical stability such that the operating arms are able to guide in situ displacement in the space of the surgical instruments in relation to the site to be treated and to do so in complete safety.

This stability of the device is such that, in practice, the operating arms act as it were as substitutes for the surgeon's hands.

However, this volume of the support in the deployed position can be compatible with the intended use of the support and, in particular, it can be adapted to the size and shape of the site to be treated in the body. This site can be the stomach, for example, but other sites within the patient's body can also be considered, and a person skilled in the art will easily adapt it as a function of the nature of these sites.

The conversion of the support from a non-deployed position to a deployed position, and the conversion, vice versa, of the support from a deployed position to a non-deployed position, is made by "extension means", which are themselves under the control of actuation means, which can be manual or automatic.

It will be noted that the notion of "extension means" as used in the present description is equivalent to the notion of "folding/unfolding device" as it appeared in the French priority application EP 04447144.9.

It is therefore be understood that the deployment of the support according to some embodiments has a reversible character.

The extension means of the device can be of different types; they can in particular be of the hydraulic, pneumatic or mechanical type.

In this context, it will further be noted that the notion of "actuation means" as used in the present description is equivalent to the notion of "actuation device" as it appeared in the French priority application EP 04447144.9.

The support is able to be connected to an endoscope only when it is in the deployed position.

In this deployed position of the support, the central opening of the ring, also called the endoscopic aperture or hole, has a shape and size compatible with connecting the device to the distal end of an endoscope.

This connecting has the particular feature of being able to be done remotely. For this reason, the connection can be done in a novel way in situ.

The connection to the endoscope is effected by remote connection devices being part of the ring.

The notion of "remote" connection reflects the particular ability of the ring, and hence of the support according to some embodiments, to be connected in situ, that is to say in the patient's body, and more precisely once the support according to some embodiments has reached the site to be treated. This technical feature distinguishes the support according to certain embodiments from many other endoscopic devices that have been described in the prior art, such as the one described in the document U.S. Pat. No. 6,352,503, B1 for which connection to the endoscope must necessarily be done outside the patient's body.

These connection means can either be specific mechanical means, for example clips, or they can be obtained indirectly by the action of certain elements of the ring fulfilling other functions. Thus, in the inflatable form of the support, the connection means can be obtained by the pressure exerted around the endoscopic aperture or hole by the fluid circulating in the ring, before introduction of the device into the patient's body.

These connection means, and more generally the configuration of the ring in the deployed position, are designed to optimize the contact surface between the ring and the endoscope, while maintaining maximum flexibility of the endoscope.

In addition, the endoscopic support according to some embodiments and more particularly the connection means are such that the connection can be made to all types of endoscopes available on the market, both for axial viewing and for lateral viewing. The endoscopic support can be adapted to a wide range of endoscopes that differ in shape, size, weight, composition, etc.

Even more generally, the endoscopic support can be adapted to a wide range of viewing systems that differ in shape, size, weight, composition, etc.

It will also be noted that the endoscopic support according to some embodiments and more particularly the connection means, the central opening of the ring and the dimensions of the ring are such that the connection of the support to an endoscope can be effected at different heights along the distal end of this endoscope, without, in doing so, compromising the flexibility of the endoscope.

The term "distal end of an endoscope" is understood as a zone of the endoscope comprising the hookable end of this endoscope, that is to say the end that can be actuated by control means such as levers, and a zone of between approximately 5 cm and approximately 10 cm upstream.

The means for connecting the device to an endoscope and the extension means of the device can be identical.

According to some embodiments, the operating arms of the device are "attachable" to the connection ring.

In other words, in the device according to some embodiments, the operating arms are attached or not attached to the connection ring, but they, in all cases, have the ability to be attached to said ring.

The operating arms are sufficiently flexible to be to be oriented by orientation means.

It will be noted that the notion of "extension means" as used in the present description is equivalent to the notion of "orientation device" as it appeared in the French priority application EP 04447144.9.

Just like the extension means, these orientation means can be of different types; they can in particular be of a hydraulic, pneumatic or mechanical type.

Just like the extension means, the orientation means of the operating arms can be actuated by actuation means of a manual or automatic type.

It will be noted that, for the support, a "deployed position of the support when not in operation" is defined as a deployed position in which the support can be connected to an endoscope and the actuation means do not function, that is to say the operating arms do not move. This deployed position corresponds to a position of rest of the support in which the operating arms are oriented substantially perpendicularly to the plane of the ring and are substantially parallel to one another.

Figure 1A:
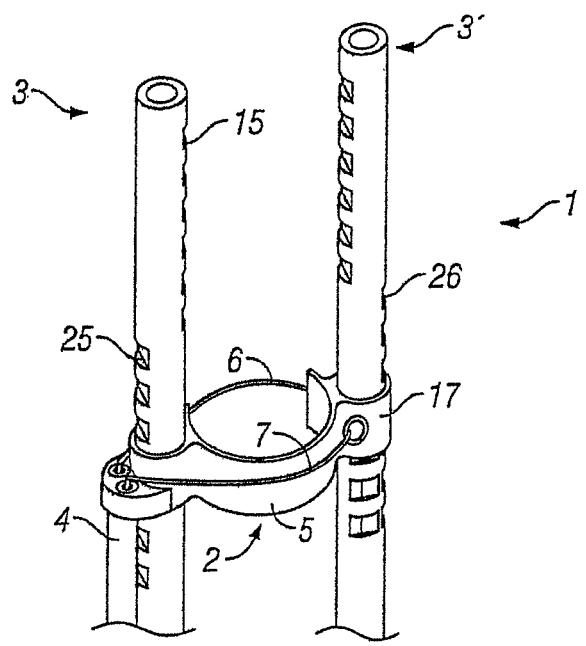
FIGS. 1a and 1b show a general view of an endoscopic support according to this embodiment, in the deployed position.

An example of one embodiment of the operating support is shown in FIGS. 1a-1-b, 2a-2b, 3a-3b.

The endoscopic support 1 comprises a connection ring or connection interface 2 designed for connection to an endoscope, and two operating arms 3, 3' attached to said connection ring 2 by attaching means 17, which may be rigid.

The operating arms 3, 3' are in the form of flexible tubes and comprise at least one lumen or channel configured in such a way that surgical tools or instruments of different shapes can be passed through them.

The endoscopic support 1 has at least two positions, namely a non-deployed position corresponding to a minimum volume of said support such that said support can be introduced into the body of a patient via natural routes (called endoluminal routes, that is to say through the mouth or anus), and a deployed position corresponding to a position of connection to the endoscope, that is to say a position in which an endoscope can be connected to the support. This position is the one that the support can adopt once it has reached its target, for example the stomach.

Extension means of the support 1 are provided for this purpose (see below).

In the connection position of the support, the connection ring 2 is deployed, whereas, in the non-deployed position of the support, this ring 2 is folded up on itself.

In this embodiment, the connection ring 2 comprises a flexible membrane 5 which contributes, together with at least one cable called the "connection cable" 6, to the shape of the ring 2 in the connection position of the support 1.

The connection ring 2 also comprises at least one cable called the "fold-back cable" 7, with which the ring 2 can be folded up when the support 1 moves from the connection position (deployed) to the non-deployed position.

The fold-back cable 7 and the connection cable 6 together form the extension means of the ring 2 and, consequently, of the support 1. This device (6, 7) can be actuated by way of rigid guides 4, made of metal or other material, which may be arranged in the area of the operating arms 3 and 3', but other equivalent means can also be provided for this purpose.

The actuation of the movement (setting in motion) of the fold-back cable 7 and the connection cable 6 of the extension means is controlled either manually or automatically by control means, by way of said rigid guides 4.

In the rest position of the support 1, the two arms 3 and 3' are oriented substantially in parallel to one another and substantially perpendicularly to the plane of the connection ring 2.

In addition, the two arms 3 and 3' are arranged opposite each other with in relation to the diameter of the ring 2.

The operating arms 3 and 3' are advantageously provided with optical markers (not shown) familiar to a person skilled in the art, to permit in situ visualization of the device, and in particular of the operating arms.

These optical markers can, for example, be in the form of radiopaque strips arranged at regular intervals along the operating arms, for example every centimeter in the last 10 centimeters of the operating arms.

According to one aspect, each of the operating arms 3 and 3' has at least two degrees of freedom, $\alpha, \gamma$ and $\alpha', \gamma'$, respectively, which correspond to two rotations in a first orientation plane defined by the two main axes B and B' of said operating arms 3 and 3', respectively. Each of the operating arms 3 and 3' can be oriented (inclined) in this first plane by a certain angle $\alpha$ and $\gamma$ (arm 3) or $\alpha'$ and $\gamma'$ (arm 3'), and independently, by virtue of an orientation device.

In other words, the arms 3 and 3' can be oriented independently of one another in at least two dimensions in space, by virtue of this orientation device.

In this embodiment, the device for orientation of the operating arms 3, 3' (also called the positioning device) comprises a set of cables 15, 25 on the one hand and 16, 26 on the other, these cables being situated respectively in the area of the operating arm 3 and of the operating arm 3' (two series of cables on each of the operating arms 3 and 3' permitting displacements in opposite directions). These cables can be actuated via mechanical or automatic control means, also called actuation means.

Generally speaking, the orientation of the operating arms 3 and 3' is adjusted by the orientation means in such a way that, when the endoscopic support is connected to the endoscope, the operating arms do not obstruct the visibility conferred by the endoscope.

It should be noted that the orientation means can be designed to orient the arms 3 and 3' with angle values $\alpha, \gamma$, $\alpha'$, $\Gamma'$ such that, under the conditions of use, when the surgical instruments 9, 10 are fixed to said arms 3 and 3', said surgical instruments 9, 10 always face each other.

Figure 1B:
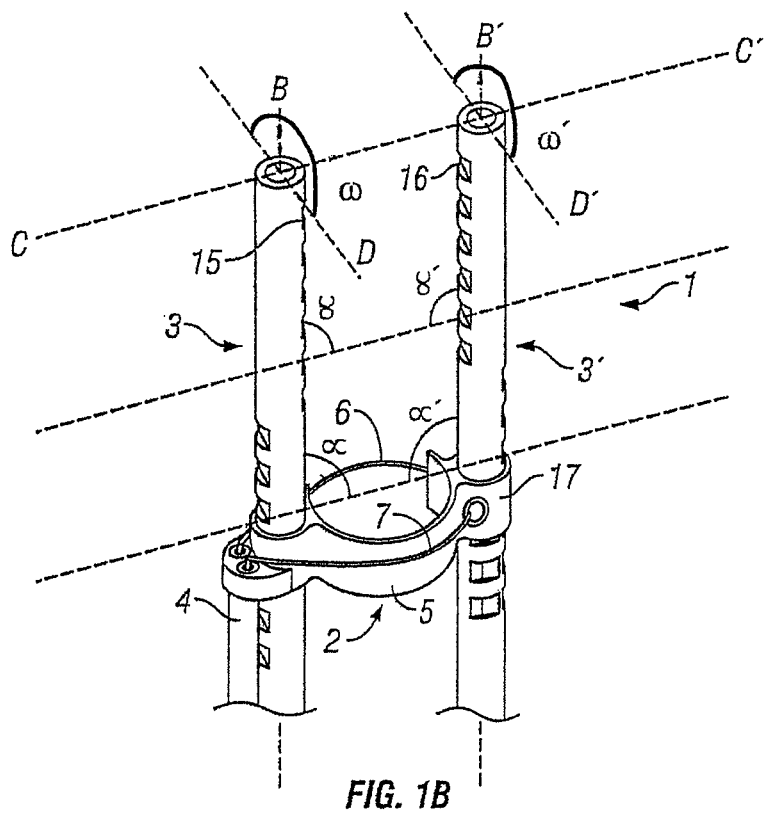
Figure 2A:
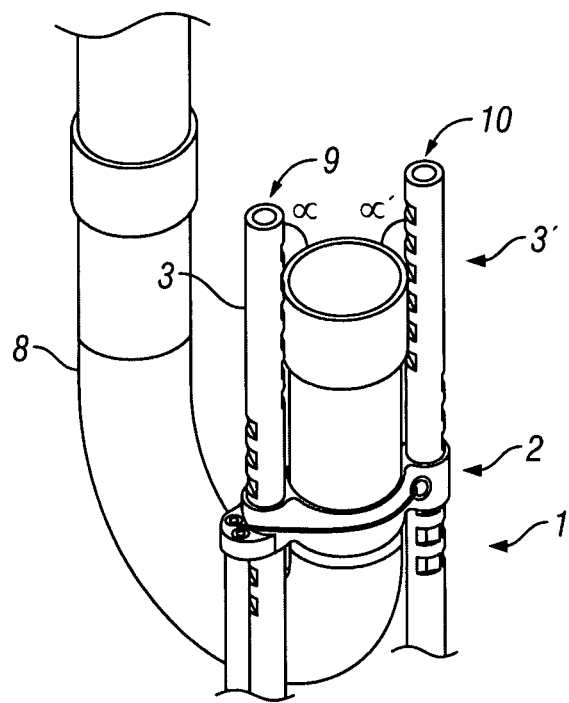
FIGS. 2a-2b show two different views of this same endoscopic support, with an endoscope connected to this support.
Figure 2B:
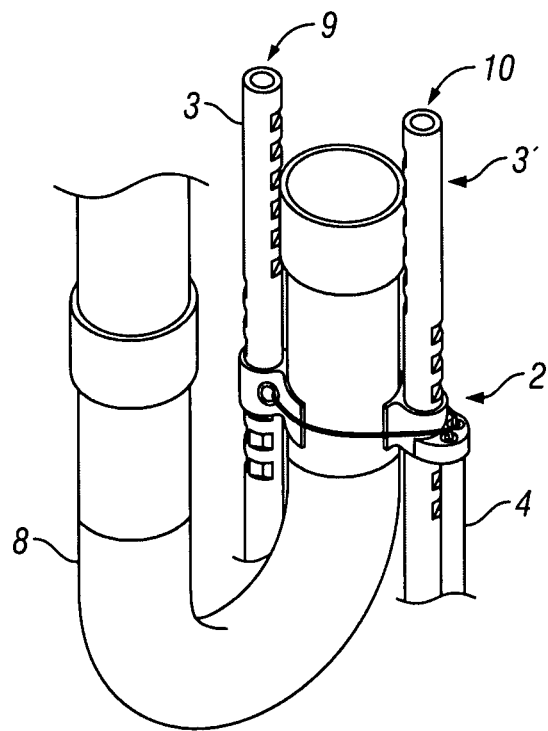
Figure 3A:
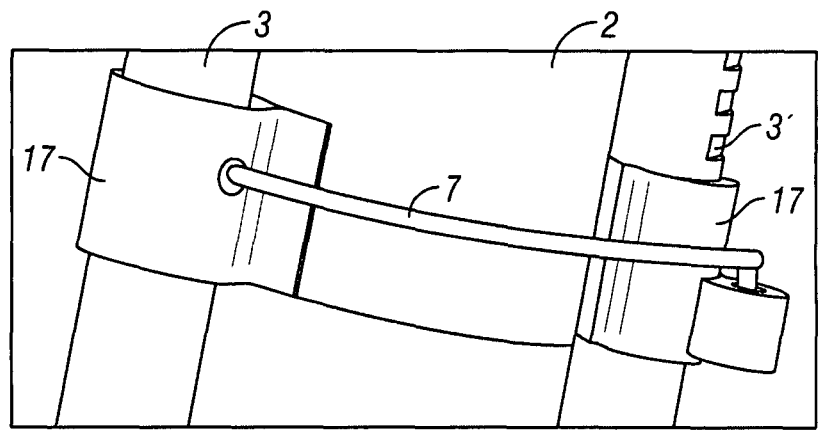
FIGS. 3a and 3b show two different views depicting in detail the connection ring for connecting to the endoscope in this embodiment of a support.
Figure 3B:
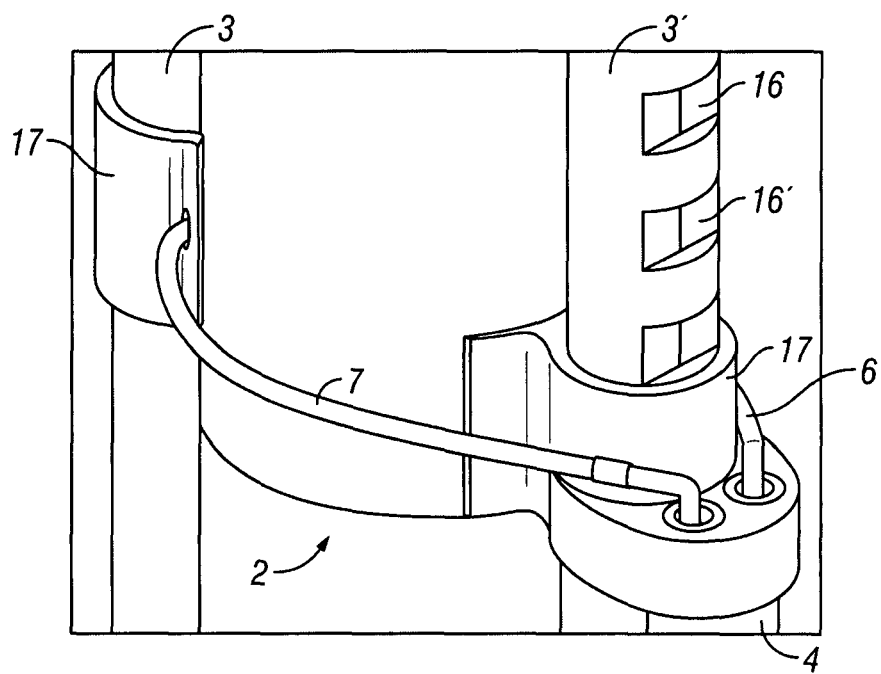

It is particularly advantageous for each of the operating arms 3 and 3' additionally to have another degree of freedom (third degree of freedom) which corresponds to a rotation in a second orientation plane defined on the one hand by the main axis B or B' of said operating arm 3 or 3' and on the other hand by a second axis D or D' corresponding to an axis perpendicular to the first orientation plane defined above. (It will be noted, as seen in FIG. 1*b*, that CBD and C'B'D' each form two rectangular trihedrons). Each of the operating arms 3 and 3' can be oriented (inclined) in this second orientation plane by a certain angle $\omega$ or $\omega'$, and independently, by means of the orientation device.

For this purpose, the means for orientation of the operating arms 3, 3' comprise additional cables 35, 45, etc. and 36, 46, etc. (not shown in the figures) which are situated in the area of the operating arms 3 and 3', respectively, and can be set in movement by mechanical or automatic control means in such a way as to orient the arms 3 and 3' specifically in the second orientation plane defined by these angles $\omega$ and $\omega'$.

In other words, the arms 3 and 3' can advantageously be oriented independently of one another in three dimensions in the space, by means of the orientation means.

Other cables can also be added in order to increase independently the mobility of the surgical instruments 9 and 10.

The operating arms 3 and 3' can also be provided with other degrees of freedom that would allow them to be oriented with still greater precision. Thus, it can be intended that the arms 3 and 3' can also be oriented in translation along their main axes, and independently of one another, and the orientation means can be adapted to this purpose.

It can also be planned to allow the operating arms to turn about themselves (about their respective main axes).

In practice, when using the operating support according some embodiments, the surgeon can proceed as follows.

The operating support 1 in the non-deployed position is introduced by an endoluminal route, for example through the mouth, into the digestive tract of the patient. Once the operating support has reached the target that is to be treated, for example the stomach or oesophagus, the surgeon manually or automatically controls the deployment of the support 1 via the actuation of the extension means. The connection ring 2, which was not deployed, then deploys. More precisely, the connection cable 6 is actuated and forms, with the flexible membrane 5, the connection ring 2 with its orifice or hole 11. The support 1 is then in its position of rest or equilibrium.

The endoscope 8 is then inserted into the aperture 11 of the connection ring 2, and surgical instruments 9 and 10 are inserted into the operating arms 3 and 3', respectively.

The orientation means are then in turn actuated via the manual or automatic control means, in such a way as to set the operating arms 3 and 3' in movement in at least two directions in the space (angles $\alpha, \gamma$ and $\alpha', \gamma'$, respectively), or in three directions in the space (angles $\alpha, \gamma$ and $\alpha', \gamma'$ on the one hand, and $\omega$ and $\omega'$ on the other hand, with possible translation of the arms 3 and 3'). The result is the precise positioning of the surgical instruments 9 and 10, respectively, in relation to the target that is to be treated and with respect to the endoscope 8.

The endoscopic support can additionally be designed to permit orientation of the surgical instruments 9 and 10 in translation in the operating arms 3 and 3' and in rotation about their axes, under actuation of the control means.

Once the instruments have been correctly positioned in this way, the surgical procedure can begin. During the procedure, the control means can actuate the orientation means for the purpose of at any time adjusting the 3D position of the operating arms 3, 3' and, consequently, of the surgical instruments 9, 10.

A safety system including alarm means can additionally be provided so that it is possible at any moment, in the event of any problem, to interrupt the procedure and, if necessary, quickly disconnect the operating support 1, the endoscope and the surgical instruments.

Once the surgical procedure has been completed, the endoscope 8 and the surgical instruments 9, 10 are removed from the operating support 1, and the extension means are once again actuated in order to fold up said support 1. The support 1, thus in the non-deployed position, can then be removed from the body of the patient.

It should be noted that the composition and dimensions of the endoscopic support 1 can be configured such that they are compatible with its use. In other words, the materials used for manufacturing the various elements of the support can be chosen from among biocompatible materials such as silicone, PTFE, PVC, PP, PS, PET polymers, stainless steel, nitinol or titanium.

The size of the connection ring 2 (thickness, height h and perimeter) will also be chosen in such a way as to optimize the contact surface with the endoscope and to thus obtain a stable and secure assembly in particular.

Similarly, regarding the manufacture of the endoscopic support according to some embodiments, different methods may be considered for manufacturing the various elements, for example injection, extrusion, laser marking, or machining.

In addition, these different elements can be assembled using different techniques, such as adhesive bonding, welding, for example ultrasound welding, or sandwich injection molding.

Moreover, it should be noted that if, in the example described above, the extension means of the connection ring 2 and hence of the support 1 comprise a set of cables joined to rigid guides 4, made of metal or other material, it is possible for other devices with the same function to be used, for example a device with internal slide, or external slide, or a device winding around an operating arm.

It will be noted that, in this embodiment, the flexible membrane 5 can be replaced by any equivalent means, for example one or more cables, as is illustrated in the second configuration (see below).

It would also be possible for the membrane 5 to be rigid instead of flexible.

FIGS. 4 to 10 illustrate another configuration, compared to the first configuration in FIGS. 1a-3b, the membrane of the connection ring has been replaced by a cable.

Figure 4:
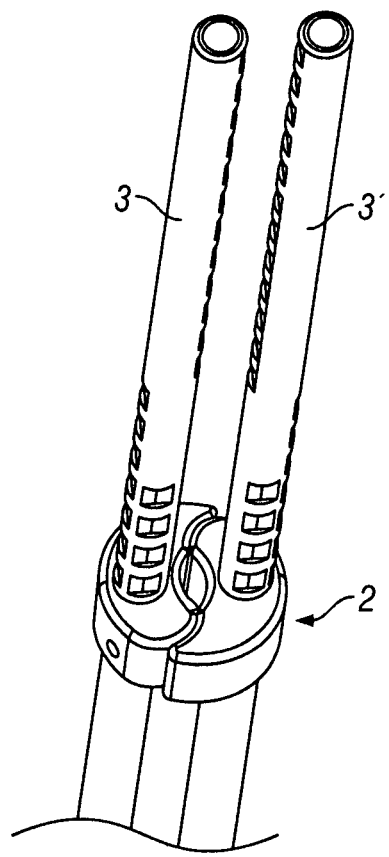
FIGS. 4 to 10 illustrate another embodiment in which, compared to the configuration in FIGS. 1a-3b, the membrane of the connection ring has been replaced by a cable.
Figure 5:
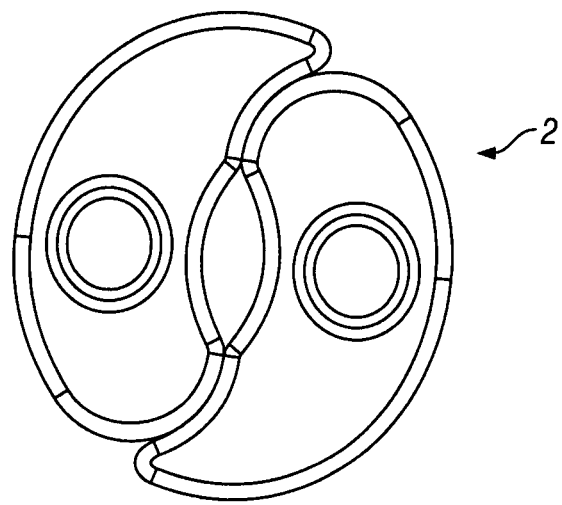

FIG. 4 (general view) and FIG. 5 (detail of the connection ring) correspond to the support without endoscope, and in the non-deployed position.

FIGS. 6 to 10 show different general and detailed views of this same support in the deployed position and connected to an endoscope.

Another embodiment of the endoscopic support is shown in FIG. 23.

In this embodiment, the connection ring or interface 2 has the form of a rigid structure capable of pivoting about the axis A, by, for example, an angle of pivoting or rotation β of approximately 90°, in such a way as to be non-deployed or, by contrast, deployed. In the deployed position, the connection ring or interface 2 has its main axis substantially perpendicular to the operating arms 3, 3'. If a north face 13 and a south face 14 are defined for the ring 2 in this position, the non-deployed position of the ring 2 corresponds then to a position of the ring in which the north face 13 and the south face 14 are this time situated in planes parallel to the operating arms 3, 3'.

In other words, when the endoscopic support 1 is in practice to be introduced into the body of a patient, for example into the oesophagus, the support 1 is not deployed and, consequently, the connection ring or interface 2 exposes its north face 13 and its south face 14 in the axis of the oesophagus.

Extension means of the ring 2 and therefore of the endoscopic support 1 with the aid of a cable connected to rigid guides, made of metal or other material, can be provided in order to bring about such a change in formation.

These extension means can be actuated by manual or automatic control means.

Figure 6:
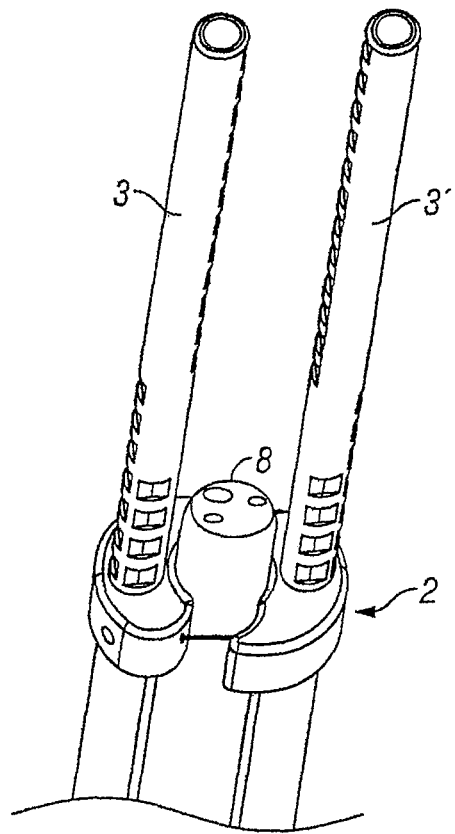
Figure 7:
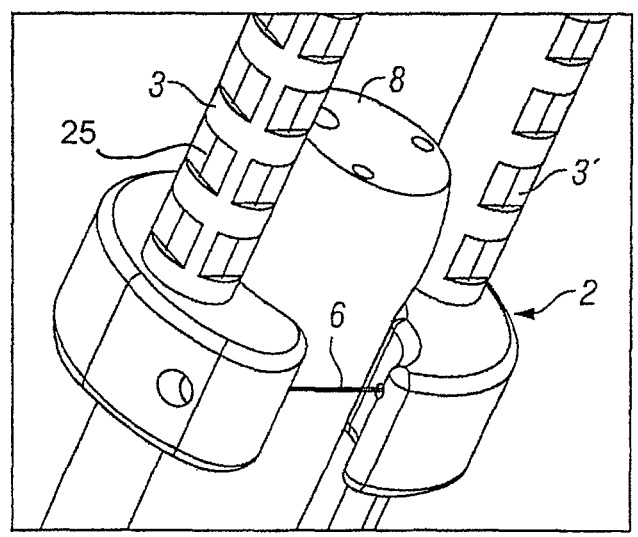
Figure 8:
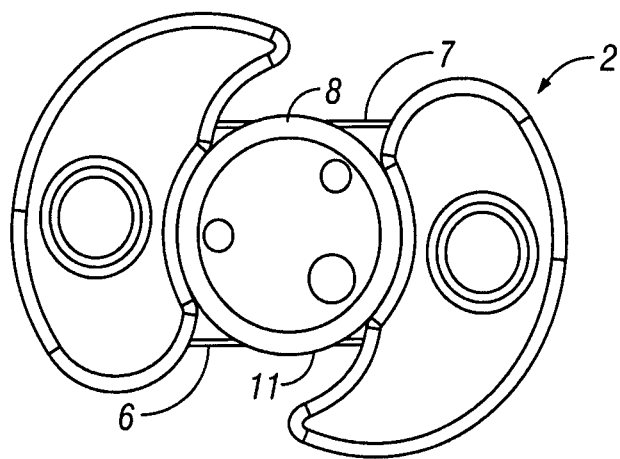
Figure 9:
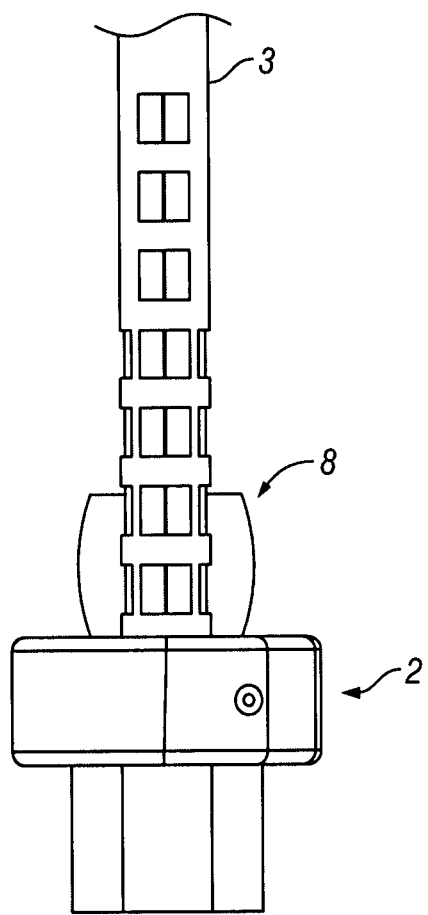
Figure 10:
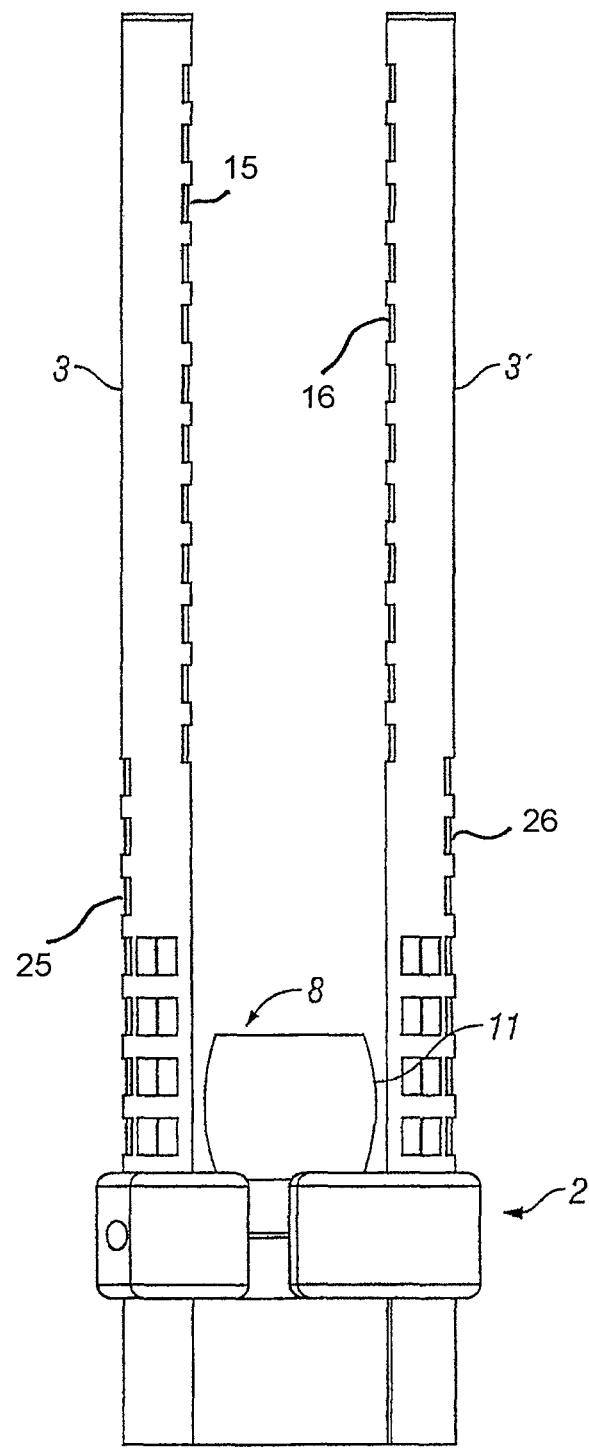

A configuration of another embodiment of the endoscopic support is illustrated in FIGS. 4 to 6.

In this configuration, the connection ring or interface 2 has the form of an inflatable structure or membrane provided, at its center, with an aperture called the "endoscopic aperture" 11, the shape of which varies as a function of the state of inflation of the membrane 2. When the membrane 2 is sufficiently inflated, the size of the endoscopic aperture 11 is such that an endoscope 8 can be fixed therein (for example by shape engagement).

The membrane 2 also comprises, within its thickness, passages 12, 12' for the operating arms 3, 3' which pass right through it, while the part of the operating arms 3, 3' situated outside the membrane 2 may be held in an endoscopic guide 18 which protects it from the environment.

Different means for inflating the membrane 2 may be considered. For example, the inflation can be obtained by circulating a pressurized fluid (liquid or gas) inside a channel or compartment for delivery of fluid.

Similarly, different orientation means of the operating arms 3, 3' may be considered. For example, the membrane can be provided with one or more channels or compartments 20 that are able to receive a pressurized fluid (liquid or gas) and are formed within the membrane 2 in such a way as to exert a greater or lesser force on the operating arms 3, 3' and thus adjust their position in three dimensions, and hence the one of the surgical instruments 9, 10.

In these cases, the support 1 and more particularly the connection ring or interface 2 are therefore connected to an external source of fluid.

FIGS. 14 to 19 also relate to this configuration. Compared to FIGS. 11 to 13, these correspond to an improved model of the support in three dimensions (FIGS. 14, 15, 18, 19) or in two dimensions (FIGS. 16, 17). In FIGS. 14 to 17, the support is deployed, but not connected to an endoscope. In FIGS. 18 and 19, the support is deployed and is connected to an endoscope.

It will be noted that FIGS. 15 to 18 show the structure of the connection ring in this embodiment.

FIGS. 20 to 22 relate to another configuration of the endoscopic support or device. This configuration differs from the first configuration in that the operating arms are at least partly curved. In FIGS. 20 and 22, the support is in the deployed position and is connected to an endoscope. In FIG. 21, the support is also deployed, but is not connected to an endoscope. FIG. 21 also shows the presence of a pocket or of compartments 21 in the area of the operating arms, these helping to form the orientation means of said arms.

Other alternative embodiments of the support 1 may be provided, for example a support with a half-ring.

As has been illustrated above, with the endoscopic support, it is possible, by virtue of the means for orientation of the operating arms 3, 3', to obtain a precise positioning of the surgical tools in the field of vision of the endoscope and at a variable angle of inclination, thus making surgical access easier.

In addition, as far as the operating arms 3, 3' are relatively flexible, the endoscopic support can be used with surgical tools of widely varying shapes, including angular (not straight) surgical tools.

Another advantage of the endoscopic support is that it is not made attached to the surgical tools or to the endoscope. Its design therefore means that it can be adapted to all types of endoscopes and of surgical tools. It is also able to be adapted to all types of viewing systems, not just endoscopes.

Even though the endoscopic support is advantageously designed to be single-use, this means that, if said support were designed to be reused, its maintenance is also facilitated both in terms of simplicity and costs and time involved.

In addition, the support is such that the surgeon has the possibility of changing the viewing system in situ, during the operation. He can thus adapt, for example first connect the support to an endoscope for lateral viewing and, during the operation, he can then change this endoscope and replace it by an endoscope for axial viewing, or vice versa.

Moreover, the support is such that the surgeon can easily change in situ the height at which the endoscope is connected to the support, thereby ensuring that the endoscope has maximum flexibility, without thereby compromising on the visibility of the surgeon.

The potential medical applications of the instrument according to these embodiments are numerous and concern in particular the treatment of diseases such as gastrointestinal reflux, morbid obesity, resection of gastric tumors, creation of anastomoses between various structures of the digestive system, and other applications besides.

Some embodiments offer a device comprising a positioning and/or orienting device for an endoscope and for surgical instruments coupled to said endoscope, which device would allow precise spatial positioning and/or orientation of said surgical instruments in relation to each other and in relation to said endoscope.

In particular, some embodiments offer a device that is compatible not only with endoluminal insertion (either oral or anal), but also with the in situ placement of the surgical instruments in the lumen of the digestive tract.

Thus, some embodiments make available a device that offers sufficient dimensional and mechanical stability for placing these surgical instruments in the lumen of the digestive tract.

Some embodiments offer a device permitting in situ placement of surgical instruments in the body of a patient at target sites other than those in the digestive tract, and in particular target sites located in the intraperitoneal cavity, for example the pancreas.

Various embodiments would thus allow a wide variety of surgical procedures to be performed by an endoluminal route, thus increasing patient comfort.

Another object of certain embodiments is to offer a device that can be adapted to a wide range of surgical instruments and endoscopes.

Some embodiments offer a device that can be adapted to a wide range of viewing systems other than endoscopes.

Some embodiments also offer a device that is easy to use and maintain, while guaranteeing maximum safety.

In conclusion, the instrument is therefore understood as a technical tool at the disposal of the surgeon in order to make it easier to perform surgical procedures such as sutures, precise incisions and resections in the context of interventional therapeutic endoscopy.

What is claimed is:

1. An adjustable endoscopic support device, comprising:
   a connection element comprising at least two members, the connection element configured to connect to an endoscope, the connection element having an opening of adjustable size such that the connection element is configured to increase the size of the opening to receive the endoscope therethrough and to decrease the size of the opening to hold the endoscope therein;
   at least two guiding elements configured to be attached to the connection element, each of the guiding elements configured to receive at least one surgical instrument;
   an orientation component for each guiding element, each orientation component configured to orient the guiding element connected thereto independently of the other guiding element in at least two degrees of freedom in rotation about two substantially parallel and spaced apart axes substantially perpendicular to a first orientation plane defined by two main axes of the guiding elements, wherein the orientation components are each configured to displace the guiding element connected thereto such that the surgical instrument is displaced in at least two dimensions; and
   an extension element coupled to the connection element and configured to control the adjustment of the opening, wherein the extension element comprises at least one cable extending between the two members to couple the members to one another, wherein actuation of the cable causes the two members to move relative to one another to adjust the size of the opening.

2. The device according to claim 1, wherein each of the guiding elements has a third degree of freedom in rotation, such that each of the guiding elements can be oriented in the third degree of freedom in a second orientation plane.

3. The device according to claim 1, wherein the second orientation plane of the guiding elements is defined by the main axis of the guiding elements and a second axis corresponding to the axis substantially perpendicular to the first orientation plane.

4. The device according to claim 1, wherein each of the guiding elements additionally has a degree of freedom in translation corresponding to the degree of freedom in translation along the main axis of the guiding elements.

5. The device according to claim 1, wherein each of the guiding elements additionally has a degree of freedom in rotation corresponding to the degree of freedom in rotation along the main axis of the guiding elements.

6. The device according to claim 1, wherein the connection element is configured to operate according to the extension element so as to selectably hold the endoscope.

7. The device according to claim 6, wherein the extension element is remotely actuatable so as to remotely adjust the size of the opening.

8. The device according to claim 1, wherein the connection element has in situ a maximum volume which is greater than a minimum volume of the connection element by at least one of at least about 10%, at least about 20%, at least about 30%, at least about 40%, at about least 50%, at least about 60%, at least about 70%, at least about 80%, at least about 90%, at least about 100%, at least about 200%, at least about 300%, at least about 500%, at least about 1000%, and at least about 2000%.

9. The device according to claim 1, wherein the guiding elements are oriented substantially perpendicularly to a plane of the opening and are substantially parallel to one another.

10. The device according to claim 1, wherein the device is configured to be coupled to a manual or automatic actuation device for controlling actuation of at least one of the orientation component and the extension element.

11. The device according to claim 1, wherein the connection element comprises at least two rigid members arranged around the opening and configured to hold the endoscope therebetween.

12. The device according to claim 11, wherein the opening is adjustable between sizes which are respectively small and large relative to one another, wherein the opening is configured to receive the endoscope theretirough when adjusted to be the large size, and the device is configured so that the rigid members are movable to reduce the size of the opening and to clamp the endoscope to the connection element.

13. The device according to claim 1, wherein each orientation component comprises a set of actuatable cables running along the guiding elements.

14. The device according to claim 1, wherein the guiding elements are flexible.

15. The device according to claim 1, wherein the guiding elements are arranged opposite each other in relation to the connection element.

16. The device according to claim 1, wherein the guiding elements comprise optical markers.

17. The device according to claim 1, wherein at least one of the guiding elements, the orientation components, and the extension element is single-use.

18. The device according to claim 1, wherein the device is configured to be cleaned and reused at least one time after cleaning.

19. An endoscopy kit comprising the endoscopic support device according to claim 1 and at least one of an automatic actuation device and a manual actuation device of at least one of the orientation components and the extension element.

20. A method for performing a surgical procedure in the body of a patient, the method comprising:
    assembling the support device and the actuation device of claim 19;
    introducing the device, in the non-deployed position, by an endoluminal route into the body of the patient to near a site to be treated;
    deploying the device in situ with the aid of the extension element;
    connecting an endoscope in situ to the device at the distal end of the endoscope;
    setting the height at the distal end of the endoscope;
    fixing one or more surgical instruments on one or more of the guiding elements;
    performing a surgical operation by controlling, via the orientation component, the in situ orientation of the guiding elements, and, consequently, the displacement of the instruments, under the control of the actuation device;
    during the operation, varying the orientation of the endoscope and the surgical instruments in relation to the site to be treated;
    once the operation has been completed, removing the surgical instruments from the endoscopic support device, disconnecting the endoscopic support device and the endoscope in situ, under the control of the extension element, converting the endoscopic support device in situ from a deployed position to a non-deployed position, and removing the endoscopic support device from the patient's body;
    taking the endoscopic support device apart; and
    at least one of cleaning the endoscopic support device and throwing away the endoscopic device.

21. An endoscopy kit comprising an endoscopic support device according to claim 1 and at least one of an endoscope and a surgical instrument.

22. The device according to claim 1, wherein the two parallel axes of rotation are located on a distal side of the connection element.

23. The device according to claim 1, wherein the guiding elements are formed of flexible tubes fixedly attached to the connection element when in use.

24. The device according to claim 1, wherein the orientation components for the guiding elements comprise first actuators connected to the guiding elements at a first position along the guiding element and at a first side of the guiding element, and second actuators connected to the guiding element at a second position along the guiding element and at a second side of the guiding element, wherein the second position is more distal than the first position and the first and second sides are opposite one another, wherein the first and the second actuators enable movement in the two rotational degrees of freedom of the guiding element about the two parallel and spaced apart axes.

25. The device according to claim 1, wherein the connection element has a height smaller than its diameter when the opening has maximal size.

26. An adjustable endoscopic support device, comprising:
    a connection element comprising at least two members arranged around an opening, wherein the members are coupled to each other so as to be movable relative to each other to adjust a size of the opening, such that the connection element is configured to increase the size of the opening so as to receive an endoscope therethrough and to decrease the size of the opening so as to hold the endoscope;
    an actuator, configured to remotely control the members movement, thereby adjusting the size of the opening, wherein the actuator comprises at least one cable, and wherein the members are coupled to each other by the cable;
    at least two guiding elements configured to be attached to the connection element, each of the guiding elements configured to receive at least one surgical instrument; and
    at least one orientation component for each guiding element, wherein each orientation component is configured to orient the guiding element connected thereto independently of the other guiding elements so as to confer on the surgical instrument a displacement in at least two dimensions.

27. The endoscopic support device of claim 26, wherein the cable surrounds at least in part the opening.

* * * * *

UNITED STATES PATENT AND TRADEMARK OFFICE
CERTIFICATE OF CORRECTION

PATENT NO. : 8,684,912 B2  
APPLICATION NO. : 11/640705  
DATED : April 1, 2014  
INVENTOR(S) : Deviere et al.

Page 1 of 1

It is certified that error appears in the above-identified patent and that said Letters Patent is hereby corrected as shown below:

Title page, column 1 item (63) (Related U.S. Application Data) at line 2, Change "Jun. 6, 2005." to --Jun. 20, 2005.--.

In the Specification

Column 1 at line 8, Change "Jun. 6, 2005," to --Jun. 20, 2005,--.

Column 8 at line 51, Change "1a-1-b," to --1a-1b,--.

In the Claims

Column 14 at line 35, In Claim 3, change "claim 1," to --claim 2,--.

Column 15 at line 10, In Claim 12, change "theretirough" to --therethrough--.

Signed and Sealed this
Fourteenth Day of October, 2014

Michelle K. Lee
*Deputy Director of the United States Patent and Trademark Office*